United States Patent [19]

Tarrson et al.

[11] 4,073,419

[45] Feb. 14, 1978

[54] THREAD STORAGE AND DISPENSING SYSTEM

[75] Inventors: Emanuel B. Tarrson; Steven Tisma, both of Stream Wood; Donald Ritch, Nile, all of Ill.

[73] Assignee: John O. Butler Company, Chicago, Ill.

[21] Appl. No.: 678,138

[22] Filed: Apr. 19, 1976

[51] Int. Cl.² .................. B26F 3/02; B65H 35/10
[52] U.S. Cl. .................................. 225/44; 225/46; 225/51; 242/129.8; 242/137.1
[58] Field of Search ............ 242/129.8, 137, 137.1, 242/138, 125.1, 125.2; 206/63.3, 63.5, 398; 132/92 R, 92 A; 225/67–73, 44–51

[56] References Cited

U.S. PATENT DOCUMENTS

| | | | |
|---|---|---|---|
| 1,179,890 | 4/1916 | Boynton et al. | 242/137.1 |
| 1,454,429 | 5/1923 | Dresser | 242/138 |
| 2,268,547 | 1/1942 | Haines | 242/137.1 |
| 2,929,541 | 3/1960 | Castelli et al. | 225/44 |
| 3,246,815 | 4/1966 | Aronson | 225/44 |
| 3,259,335 | 7/1966 | Rosen | 242/129.1 |

Primary Examiner—Leonard D. Christian
Attorney, Agent, or Firm—Laff, Whitesel & Rockman

[57] ABSTRACT

A spool of thread, such as dental floss, is housed in a two-part shell or holder, preferably made of plastic. The floor on the bottom one of the shell parts includes a platform to provide a bearing surface for enabling rotation of the spool with a minimum of friction. The top of the upper shell part includes at least one finger which depends far enough to drag, with predetermined friction, against the top of the spool. This friction is sufficient to prevent a random unwinding of the spool and yet small enough to preclude any substantial impedance to the withdrawal of a desired amount of thread from the spool.

10 Claims, 5 Drawing Figures

THREAD STORAGE AND DISPENSING SYSTEM

BACKGROUND OF THE INVENTION

This invention relates to holders for spools of thread and more particularly to such holders including a clutch mechanism for preventing unwanted rotation or unwinding of the spool, while enabling a withdrawal of a predetermined amount of such thread responsive to a predetermined pulling force.

The term "thread" is used herein as a generic term to designate any suitable thread, string, twine, rope or the like. It is presently thought that dental floss is the specific thread that is most likely to be stored in the holder.

Holders of the inventive type for spools of thread have many uses, one of which is to hold a relatively large supply of dental floss. The general characteristics of such a holder usually requires an almost instantaneous removal of any selected length of thread, a means for cutting and holding the cut end of thread, and a means for securing the spool to prevent it from rotating or unwinding when the thread is not being removed therefrom.

In addition, when the thread is dental floss, the entire package is capable of being as small as possible for the length of enclosed thread so that it may be carried about in a pocket or purse, with a minimum of inconvenience. Beyond this, the holder should be attractive, to present a maximum sales appeal. It should also be of a shape and size which is easy for a person to manipulate, even when such person does not have normal dexterity.

Accordingly, an object of the invention is to provide a new and improved holder and packaging system for a spool of thread. Here an object is to provide a holder which can be made almost as small as the maximum sized spool likely to be used in the holder. Further, an object is to give ready access to almost any desired length of the thread, while restraining the spool to prevent an unwanted unwinding.

Another object of the invention is to provide a basic design and form of thread holder which has general utility for virtually any size of spool or thread, and yet meets the specific needs of a dental floss holder. Here, an object is to provide a holder at a minimum cost.

In keeping with an aspect of the invention, these and other objects are accomplished by providing a housing in the form of a two part shell, made of plastic or other suitable material. One part of the housing shell includes a platform to enable a rotation of the spool with a minimum amount of friction between the spool and the shell. The other part of the housing shell includes at least one finger which depends far enough to drag, with predetermined friction, against the top of the spool. This friction is great enough to prevent an unwanted and random unwinding of the spool of thread and yet small enough to preclude any substantial opposition to a desired withdrawal of thread.

DESCRIPTION OF THE DRAWINGS

The nature of a preferred embodiment of the invention may be understood from the attached drawings, wherein.

DESCRIPTION OF THE PREFERRED EMBODIMENTS

Figure 1:
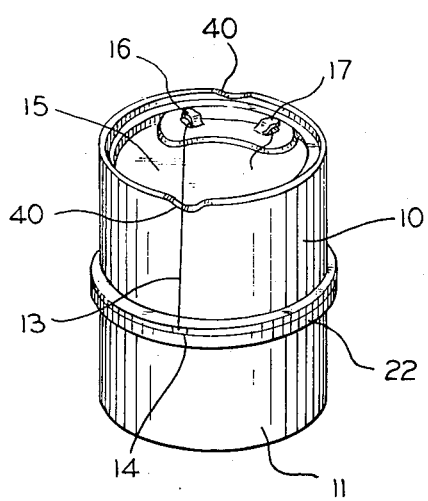
FIG. 1 is a perspective view of the inventive thread holder.
Figure 2:
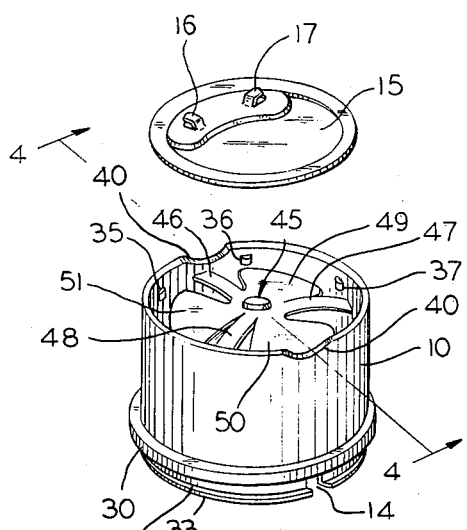
FIG. 2 is a perspective and exploded view of the holder of FIG. 1 and of the spool of thread enclosed therein.
Figure 2:
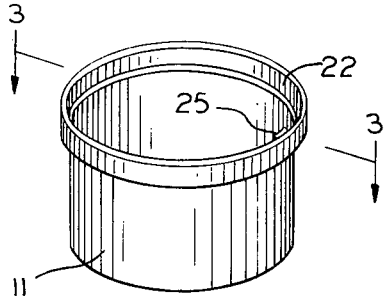

One embodiment of the inventive thread holder is shown in FIG. 1. This holder is especially adapted to store and dispense dental floss. The holder comprises upper and lower holder shells or parts 10, 11, each of which has a generally cylindrical shape. A spool or ball 12 of thread (especially dental floss) is enclosed within the holder, with the loose end 13 of the thread leaving the holder through hold or opening 14. A top closure plate 15 closes the upper holder part 10 and has at least one semi-pierced detent 16 formed thereon for cutting and anchoring the loose end 13 of the thread. In this example, there are two such detents 16, 17 on closure plate 15.

Figure 3:
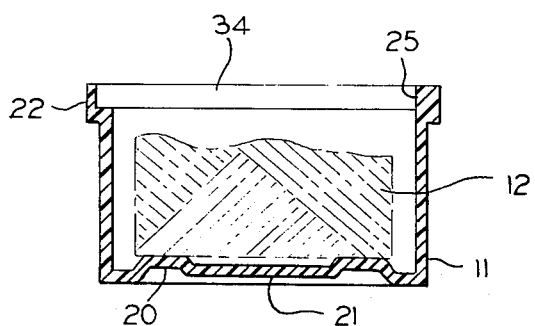
FIG. 3 is a cross-sectional view of the lower housing part taken along line 3—3 of FIG. 2.
Figure 5:
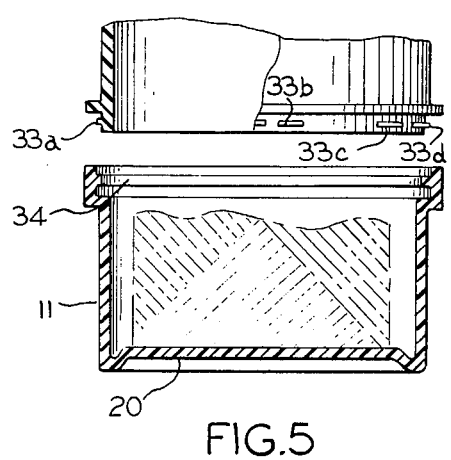
FIG. 5 is a cross-sectional view, similar to FIG. 3, showing an alternative lower housing part.

The lower holder shell or part 11 (FIGS. 3, 5) comprises a generally cylindrical container having an embossed bottom which provides a raised platform 20. The central section 21 of the raised platform 20 may or may not be depressed as shown in FIG. 3. The depression 21 provides a relatively small upstanding area 20 forming a minimum bearing surface of reduced friction between the spool 12 and part 11. The platform 20 may be smooth and unbroken, as shown in FIG. 5. The selection between these two designs of platform 20 depends largely upon the size and dimension of the spool 12 after substantial amounts of thread have been unwound from it. When the spool or ball 12 becomes small, it should not drop into the recess formed by the dpression 21. Hence, the diameter of the depressed center section 21 or bottom 20 will depend upon the diameter of the center hole 23 in spool 12.

The rim or top of the lower shell part flares outwardly (at 22) and extends cylindrically upwardly. Therefore, an enlarged circumferential space 22 is provided in lower part 11 for telescopingly receiving the bottom of the upper part 10. The outwardly flared cylindrical section 22 includes a key or embossment 25 which fits into hole 14, for indexing the upper and lower parts 10, 11, when they are snapped together.

Figure 4:
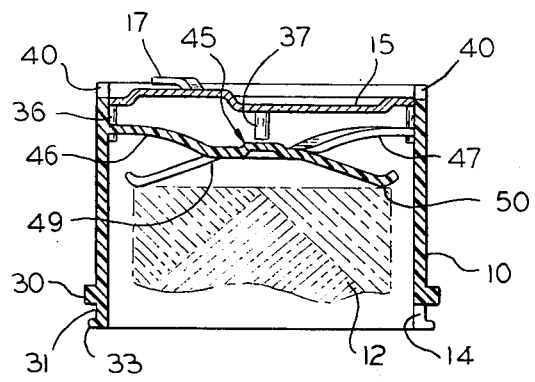
FIG. 4 is a cross-sectional view of the upper housing part taken along line 4—4 of FIG. 2.

The upper part 10 (FIG. 4) comprises a generally cylindrical member having a diameter which is substantially the same as the diameter of the lower part 11. As shown in FIG. 4, the lower edge of upper part 10 has a bead 30 which is approximately the same diameter as the flared cylindrical section 22 on the top of the lower part. Dependent below the bead 30 is a neck 31 of reduced diameter and a gripping portion 33 of slightly larger diameter. In FIG. 4, the gripping portion 33 is an annular bead surrounding the circumference of member 10. In FIG. 5, the gripping portions are a number of discrete tabs or fins 33a–33d.

The lower portion 11 has an internal circumferential outwardly projecting bead 34 within the flared cylindrical area 22 which snaps over the gripping portion 33 of the upper part 10 shown in FIG. 4. The proportions are such that the dependent sections 31 and 33, shown in FIG. 4, slip with friction inside the cylindrical section 22 (with parts 33, 34 snapping over each other) until bead 30 comes to rest on top of the part 22. When connected, the parts 10 and 11 resist separation, so that it is difficult to separate the holder without prying apart the upper and lower parts. Similarly, the upper part shown in FIG. 5 snaps into place into the lower part 11, the fins 33a–33d and bead 34 snapping over each other.

To provide greater resistance to separation, parts 10 and 11 may be connected by sonic welding.

The upper interior surface of cylindrical part 10 contains a number of circumferentially spaced embossments, e.g., 35, 36, and 37, for establishing an upper stop position. Thus, the closure plate 15 may be pressed into the top of upper part 10, to rest on the spaced embossments in a position which is substantially perpendicular to the axis of the cylinders formed by the spool 12 and holder parts 10, 11.

At one or two points 40 in the upper rim of the part 10, there is a depression or cut out which enables the loose end 13 of the thread to be brought under a semipierced detent 16, 17 and to be cut and anchored.

It should now be apparent that a spool 12 of thread (especially dental floss) may be placed inside a holder having internal contours which are almost the same shape as, and only slightly larger than the spool. Thus, there is virtually no wasted space or undue amount of bulk, either inside or outside the housing.

Inside the top portion of the upper part 10 is a spider assembly 45 forming a clutch for preventing any unwanted or random unwinding of the spool 12. Preferably, this spider 45 is integrally molded into the housing itself, although it could also be a separate piece part which is snapped into position.

The spider assembly 45 preferably includes three bowed arms 46, 47, 48 which extend from the internal cylindrical periphery of part 10 to the center thereof. Intermediate these three arms 46, 47, 48 are three dependent fingers 49, 50, 51 which extend downwardly far enough to engage and bear against the top surface of the spool 12. The ends of the fingers curve gently upwardly in all directions to avoid snagging the thread as the spool or ball turns. The friction between fingers 49, 50, 51 and the top of the spool 12 is sufficient to prevent unwanted or random rotation and unwinding of the spool 12 while enabling a quick and easy withdrawal of the thread.

In operation, the spool 12 rests with slight friction between bearing surface 20 and fingers 49, 50, 51. The loose end 13 of thread leaves the spool 12, passes out of the holder through hold 14, over depression 40, and under the semi-pierced detents 16 and 17. When the loose end is pulled away from the semi-pierced detents 16, 17, any desired amount of thread 13 may be unwound by pulling against the frictions of fingers 49, 50, 51. After the desired amount of thread 13 has been extracted from the holder, the loose end 13 is brought over the depression 40 and under one or both semipierced detents 16, 17, where a sharp edge cuts the thread and anchors the resulting loose end.

To prevent the thread on spool 12 from contacting the spider assembly 45, the thread may be wound on a core 52, which may be extended slightly above the thread on spool 12. This gives a consistent drag regardless of how much thread is unwound from the core.

Those who are skilled in the art will readily perceive how changes and modifications may be made in the inventive structure. Therefore, the appended claims are to be construed broadly enough to cover all equivalent structures falling within the scope and the spirit of the invention.

I claim:

1. A thread holder comprising a two part shell, one part of the holder shell including a raised platform to enable a rotation of a spool inside said holder with a minimum amount of friction between the spool and the holder, and the other part of the holder shell comprising an integral dependent part which is shaped and dimensioned for contacting and resiliently dragging with predetermined friction against the top of the spool, the friction being great enough to prevent an unwanted and random unwinding of the spool of thread and yet small enough to preclude any substantial opposition to a desired withdrawal of thread.

2. The holder of claim 1 wherein each of said parts comprises a generally cylindrical container molded from plastic, said containers snapping together at their open ends.

3. The holder of claim 2 wherein the rim of one part flares outwardly to form a cylindrical section and the rim of the other part telescopingly fits into said cylindrical section, and an opening formed in the rim of at least one of said parts to enable the thread to pass out of said holder.

4. The holder of claim 3 wherein one of said parts is closed by a closure plate having at least one semipierced detent formed thereon for cutting and anchoring the thread.

5. The holder of claim 4 wherein the dragging means includes at least one finger.

6. A thread holder comprising a two part shell, each of said parts comprises a generally cylindrical container having an open end, said containers snapping together at their open ends, the rim of one of said parts flaring outwardly to form a cylindrical section and the rim of the other of said parts telescopingly fitting into said cylindrical section, an opening formed in the rim of at least one of said parts to enable the thread to pass out of said holder, one of said parts being closed by a closure plate having at least one semipierced detent formed thereon for cutting and anchoring the thread, the other of said parts including a platform for supporting one end of a spool to enable a rotation of said spool inside said holder with a minimum amount of friction between the spool and the holder, and said one part including means for contacting and dragging with predetermined friction against the top of the spool, the friction being great enough to prevent an unwanted and random unwinding of the spool of thread and yet small enough to preclude any substantial opposition to a desired withdrawal of thread, said dragging means comprises a spider assembly including a plurality of arms interspersed with a plurality of fingers spaced around the circumference of the part in which said assembly is positioned, one of said fingers being disposed between each adjacent pair of said arms and adapted to drag with predetermined friction against the top of the spool.

7. The holder of claim 6 wherein each of said fingers curves gently upwardly in all directions to avoid snagging the thread as the spool turns.

8. A thread holder comprising a two part shell, one part of the holder shell including a platform to enable a rotation of a spool inside said holder with a minimum amount of friction between the spool and the holder, and the other part of the holder shell including means for contacting and dragging with predetermined friction against the top of the spool, the friction being great enough to prevent an unwanted and random unwinding of the spool of thread and yet small enough to preclude any substantial opposition to a desired withdrawal of thread, said dragging means comprises a spider assembly including a plurality of arms interspersed with a plurality of fingers spaced around the circumference of said other part, one of said fingers being disposed between each adjacent pair of said arms.

9. The holder of claim 8 wherein said spider assembly and said other part are integrally molded from plastic.

10. The holder of claim 9 wherein each of said fingers curves gently upwardly in all directions to avoid snagging the thread as the spool turns.

* * * * *